United States Patent
Canzi et al.

(10) Patent No.: US 6,380,385 B1
(45) Date of Patent: Apr. 30, 2002

(54) PROCESS FOR THE PREPARATION OF PURE MELAMINE

(75) Inventors: Lorenzo Canzi, Milan (IT); Gerhard Coufal, Leonding; Martin Müllner, Linz, both of (AT)

(73) Assignee: Agrolinz Melanin GmbH, Linz (AT)

( * ) Notice: Subject to any disclaimer, the term of this patent is extended or adjusted under 35 U.S.C. 154(b) by 0 days.

(21) Appl. No.: 09/839,199

(22) Filed: Aug. 13, 2001

Related U.S. Application Data

(63) Continuation of application No. 09/612,941, filed on Jul. 10, 2000, now abandoned, which is a continuation of application No. 09/414,633, filed on Oct. 8, 1999, now abandoned, which is a continuation-in-part of application No. 09/011,183, filed as application No. PCT/EP96/05389 on Dec. 6, 1996, now abandoned.

(30) Foreign Application Priority Data

Dec. 7, 1995 (AT) ............................................. 1994/95

(51) Int. Cl.⁷ ...................... C07D 251/62; C07D 251/60
(52) U.S. Cl. ...................................... 544/203; 544/201
(58) Field of Search .................................. 544/201, 203

(56) References Cited

U.S. PATENT DOCUMENTS

| | | | | |
|---|---|---|---|---|
| 3,116,294 A | 12/1963 | Marullo et al. | .......... | 260/249.7 |
| 3,637,686 A | 1/1972 | Kokubo et al. | .......... | 260/249.7 |
| 4,565,867 A | 1/1986 | Thomas et al. | .............. | 544/201 |
| 5,514,796 A | 5/1996 | Best et al. | .................. | 544/201 |
| 5,514,797 A | 5/1996 | Best et al. | .................. | 544/201 |
| 5,721,363 A | 2/1998 | Canzi et al. | ................. | 544/207 |

FOREIGN PATENT DOCUMENTS

| | | |
|---|---|---|
| EP | 0 808 836 | 11/1997 |
| WO | 97/34879 | 9/1997 |
| WO | 97/47609 | 12/1997 |
| WO | 98/04533 | 2/1998 |
| WO | 98/08808 | 3/1998 |
| WO | 98/27071 | 6/1998 |
| WO | 98/32731 | 7/1998 |
| WO | 98/52928 | 11/1998 |
| WO | 98/54160 | 12/1998 |
| WO | 98/55465 | 12/1998 |
| WO | 98/55466 | 12/1998 |
| WO | 98/00374 | 1/1999 |
| WO | 99/19310 | 4/1999 |

*Primary Examiner*—Mukund J. Shah
*Assistant Examiner*—Venkataraman Balasubramanian
(74) *Attorney, Agent, or Firm*—Wenderoth, Lind & Ponack, LLP

(57) ABSTRACT

A process for the preparation of pure melamine, in which liquid, ammonia-containing melamine is rapidly depressurized from an ammonia partial pressure $p_1$ between 400 and 50 bar to an ammonia partial pressure $p_2$ between 200 bar and atmospheric pressure, where $p_1$ is always greater than $p_2$, at a temperature which is 0 to 60° C. higher than the melamine solidification point dependent oil the particular prevailing ammonia partial pressure, higher pressures permitting a greater temperature interval from the melamine solidification point than lower pressures, by which means pure melamine separates out in solid form, whereupon, in any sequence, the product is further depressurized if appropriate to atmospheric pressure, cooled to room temperature and the pure melamine is isolated.

21 Claims, 1 Drawing Sheet

PROCESS FOR THE PREPARATION OF PURE MELAMINE

Figure 1:
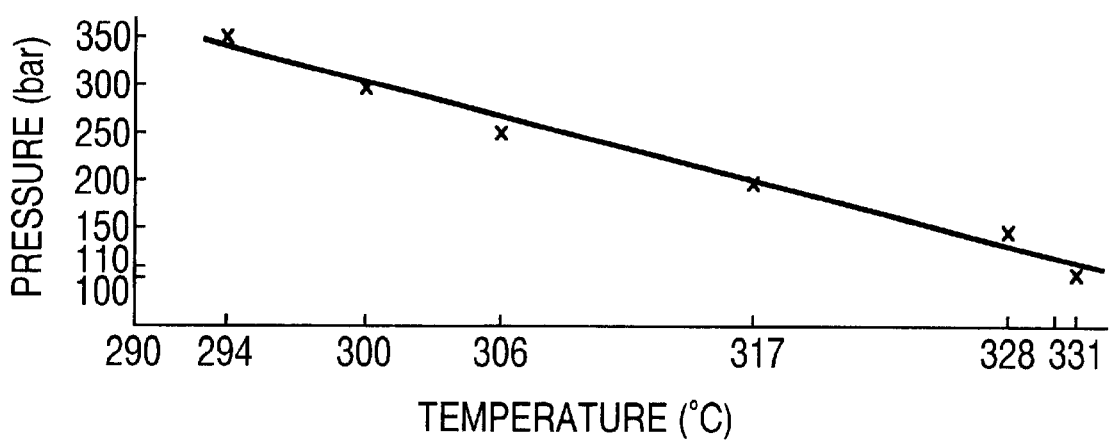

This is a continuation of Ser. No. 09/612,941, filed Jul. 10, 2000, now abandoned, which is a continuation of Ser. No. 09/414,633, filed Oct. 8, 1999, now abandoned, which is a continuation-in-part of Ser. No. 09/011,183, filed Sep. 23, 1998, now abandoned, which is a 371 of PCT/EP96/05389, filed Dec. 6, 1996.

A multiplicity of processes for the preparation of melamine are already published in the literature. A preferred starting material in these is urea, which is reacted either at high pressure and non-catalytically or at low pressure and using a catalyst to form melamine, ammonia and $CO_2$.

Although the known high-pressure processes, for instance those of Melamine Chemicals, Montedison or Nissan, in which the melamine is first formed as a liquid, have a lower energy consumption in comparison to low-pressure processes, if no purification stages are present, melamine contains impurities such as melam, melem, ammeline, ammelide or ureidomelamine, which interfere with some further melamine processing operations.

Melamine prepared by a high-pressure process is worked up, for example, according to U.S. Pat. No. 4,565,867 (Melamine Chemicals) by separating off the $CO_2$ and $NH_3$ waste gases from the liquid melamine, the pressure and temperature preferably being maintained at the same values as in the reactor. The liquid melamine is then fed to a product cooling unit, in which it is depressurized from 105–175 bar to about 14–42 bar and at the same time rapidly cooled and quenched with liquid ammonia from 350–430° C. to 48–110° C., by which means melamine separates out as a solid product.

According to U.S. Pat. No. 3,116,294 (Montecatini), the $CO_2$ and $NH_3$ waste gases are likewise separated off first, the liquid melamine is treated in countercurrent with $NH_3$ to remove $CO_2$ still dissolved, and the product is collected in a further reactor and allowed to dwell therein for a defined time. Finally, melamine is taken off from the second reactor and rapidly cooled by quenching with water or by mixing with cold gases.

However, the purity of melamine which is produced by one of these processes is insufficient for many applications, for instance in the preparation of melamine-formaldehyde resins for surface coatings, since, in particular, the melem content is too high.

According to U.S. Pat. No. 3,637,686 (Nissan), the crude melamine melt obtained by thermal decomposition of urea is rapidly cooled to 200–270° C. with liquid $NH_3$ or cold $NH_3$ gas, and is further cooled in a second step to 100–200° C. with aqueous $NH_3$ solution. The product must then be recrystallized in order to achieve a satisfactory melamine purity.

The object of the present invention was therefore to find a process which enables the preparation of pure melamine having a purity of up to greater than 99.8% and having a markedly reduced content of impurities, particularly melem and melam.

Unexpectedly, this object was able to be achieved by a process in which liquid, ammonia-containing melamine is rapidly depressurized at a temperature at or just above the solidification point of melamine dependent on the particular prevailing ammonia partial pressure, the solidification point, depending on the temperature at the beginning of depressurization and the desired final pressure, increasing by about up to 60° C., and solid melamine separating out.

The present invention therefore relates to process for the preparation of pure melamine, which comprises liquid, ammonia-containing melamine being rapidly depressurized from an ammonia partial pressure $p_1$ between 400 and 50 bar to an ammonia partial pressure $p_2$ between 200 bar and 20 bar, where $p_1$ is always greater than $p_2$, at a temperature which is 0 to 60° C. higher than the melamine solidification point dependent on the particular prevailing ammonia partial pressure, higher pressures permitting a greater temperature interval from the melamine solidification point than lower pressures, by which means pure melamine separates out in solid form, whereupon, in any sequence, the product is further depressurized if appropriate to atmospheric pressure, cooled to room temperature and the pure melamine is isolated.

The process according to the invention is suitable for the purification of melamine which is produced in any known process of the prior art and, in particular, contains impurities such as melem and melam, the melamine being able to be present either as melt or in the liquid phase or in crystalline form.

If the melamine to be purified is already present as melt or as liquid phase, such as downstream of a high-pressure reactor for the synthesis of melamine by conversion of urea, the pressure and the temperature of the melt or the liquid melamine are brought to the initial ammonia partial pressure desired for the depressurization between about 400 and 50 bar, preferably between about 400 and 80 bar, particularly preferably between about 300 and 100 bar, and to the corresponding above-defined temperature, i.e. to a temperature which is about 0 to 60° C., preferably about 0 to 40° C., particularly preferably about 0 to 20° C., above the melamine solidification point dependent on the particular prevailing ammonia partial pressure. In this process it must be noted that at higher pressures the temperature difference between melamine solidification point and the temperature to be set at the beginning of depressurization can be greater than at lower pressures, since the solidification point of the melt at higher pressures is at lower temperatures than at low pressures. In order to achieve the temperature desired for the depressurization, the temperature is decreased if necessary. The temperature is particularly preferably below about 350° C. Cooling can be carried out either rapidly or slowly. Preferably, it is performed slowly at a cooling rate of 0.8 to 10° C./min. Since the melamine melt can absorb more ammonia at a lower temperature, ammonia is preferably fed during this operation. It is particularly advantageous to depressurize the liquid ammonia-containing melamine as far as possible close to or above the melamine solidification point dependent on the particular prevailing ammonia partial pressure.

It is further possible by means of the present invention to purify solid, contaminated melamine. The melamine to be purified, which is present in crystalline form or as powder, is first heated at an ammonia partial pressure between about 400 and 50 bar, preferably between about 400 and 80 bar, particularly preferably between about 300 and 100 bar, to a temperature which is about 0 to 60° C., preferably about 0 to 40° C., particularly preferably about 0 to 20° C., above the melamine solidification point dependent on the particular prevailing ammonia partial pressure. To melt solid melamine reliably, it is expedient firstly to heat it to about 370° C. and then to cool it to the desired depressurization temperature to ensure that the melamine is completely molten. Preferably, the desired depressurization temperature is below about 350° C.

Again it must be noted that the temperature difference at higher pressures can be greater than at lower pressures.

Preferably, the process of the invention is carried out directly after a melamine high-pressure process. Examples of high-pressure processes are, for instance, the Melamine Chemical, Montedison or Nissan process, as described, for example, in Ullmann's Encyclopedia of Industrial Chemistry, 5th Edition, Vol. A16, pp. 174–179. According to these processes, urea is usually converted in a temperature range from about 370 to 430° C. and at a pressure of about 70 to 300 bar. The melamine formed in these processes is finally obtained as a liquid phase.

According to the process of the invention, the initial ammonia partial pressure desired for the rapid depressurization is, if necessary, set between about 400 and 50 bar. In order to set the corresponding initial temperature for the depressurization, the liquid melamine obtained from the urea conversion process is cooled from the temperature prevailing in the reactor by means of suitable cooling apparatuses, for instance by means of heat exchangers, to the appropriate value, i.e. to a temperature which is about 0 to 60° C., preferably about 0 to 40° C., particularly preferably about 0 to 20° C.; above the melamine solidification point dependent on the particular ammonia partial pressure set. Cooling can be performed in this process in any manner either rapidly or slowly. Preferably, the cooling is carried out at a rate which is between about 0.8° C./min and 10° C./min, preferably with further ammonia being fed in. The temperature can also be decreased by means of a cooling program, in which, for example, cooling and holding phases or different cooling rates may alternate.

Prior to cooling, the $NH_3/CO_2$ gas mixture formed in the reaction is separated off from the liquid melamine and the $CO_2$ dissolved in the liquid melamine is reduced by introducing gaseous ammonia. It is further possible to allow the liquid melamine, prior to the depressurization, to dwell for from about 5 minutes up to 20 hours at the ammonia partial pressure set. Preferably, it is allowed to dwell for between 10 minutes and 10 hours, particularly preferably between 30 minutes and 4 hours. Longer dwell times are also possible if desired.

The ammonia-containing melamine to be purified is present in liquid form prior to the depressurization. In the depressurization, the pressure is rapidly decreased, depending on the initial pressure set, to a value between 20 bar and about 200 bar, preferably to between 20 bar and about 150 bar, particularly preferably to between 20 bar and about 50 bar.

In the depressurization, the ammonia dissolved in the melamine escapes, which increases the solidification point of the melamine then substantially treed from ammonia by up to about 60° C., so that the liquid melamine immediately solidifies, and the formation of byproducts, in particular melem, is prevented. On the one hand, owing to the depressurization, the temperature in the system decreases, but on the other hand, owing to the melamine solidification, heat of crystallization is released. It is assumed that the process proceeds approximately autothermally overall.

It is advantageous if the melamine melt is saturated with ammonia before the depressurization. However, it is also possible to carry out the depressurization using a melamine melt not saturated with ammonia, but the advantage of the melting point elevation cannot be completely exploited in this case.

The depressurization can be performed directly in the vessel or the apparatus into which the liquid melamine was introduced. However, the depressurization can also be carried out by transferring or spraying melamine into one or more further vessels by means of suitable spraying apparatuses. Preferably, in this case, an ammonia atmosphere is present in the vessel. Furthermore, it is particularly advantageous to depressurize the melamine into a vessel in which approximately the same temperature prevails as in the receptacle from which it is depressurized.

The then solid melamine can, if desired, be kept at the then prevailing ammonia partial pressure and the prevailing temperatures for some further time, for instance for from 1 minute to 20 hours. Preferably, the solid melamine is allowed to dwell under these conditions for between 10 minutes and 10 hours, particularly preferably for between 30 minutes and 3 hours. Preferably, the temperature in this case should be below about 290° C. Particularly preferably, the then solid melamine is allowed to dwell at a temperature between about 280° and 250° C., the temperature during this period being able either to be kept constant or to be varied continuously or discontinuously. Subsequently to this depressurization process or the dwell time, the then solid melamine can, in any manner and depending on the technical condition, be initially cooled to room temperature and then further depressurized to atmospheric pressure or simultaneously, or in reverse order, can be further depressurized and cooled. Preferably, the solid melamine is firstly further depressurized and then cooled to room temperature.

The already solid melamine is cooled to room temperature, for example, by quenching with a cold, liquid medium, for instance by means of liquid ammonia, by mixing with cold gases, by cooling by means of heat exchangers, for example by means of a temperature program, or by simple removal of the heating medium.

The process of the invention can be carried out, as required, either in a discontinuous process or in a continuous process. It is particularly advantageous to carry out the process of the invention continuously.

In an advantageous embodiment, after separating off $NH_3$ and $CO_2$, the melamine melt is allowed to dwell at an ammonia pressure of about 70–300 bar, preferably at the prevailing reactor pressure, the temperature is decreased, with further feed of ammonia, as close as possible to the solidification point prevailing at this ammonia partial pressure, then depressurized to about 50 bar to 20 bar, if appropriate allowed to dwell, and further depressurized and cooled to room temperature.

The individual steps of the process of the invention, such as if appropriate separating off an $NH_3/CO_2$ gas mixture with if appropriate subsequent reduction of dissolved $CO_2$ content if appropriate allowing to dwell and cooling to the depressurization temperature depressurization if appropriate allowing to dwell in the solid state if appropriate further depressurization to atmospheric pressure and cooling to room temperature, can be carried out, for example, in separate vessels or apparatuses suitable for the particular step. However, it is also possible to carry out two or more of these steps in shared apparatuses. The process procedure must, however, be matched to the particular conditions.

In order to determine the dependence of the melamine solidification point on the prevailing ammonia partial pressure, appropriate cooling experiments were carried out.

Melamine is obtained by the process of the invention in crystalline form or as a powder having a purity of up to greater than 99.8 and has a markedly decreased content, in particular, of melem and melam.

EXAMPLES 1–6

Determination of the melamine solidification point dependent on the ammonia partial pressure.

9.9 g of melamine containing 0.1 g of melem were weighed into an autoclave together with the amount of ammonia required to set a defined pressure p, and melted. The reaction mixture was allowed to dwell at 370° C. for some hours h, in order to enable establishment of equilibrium. The reaction mixture was then allowed to cool and the temperature course was monitored, the solidification point being recognizable by a brief temperature increase. The process parameters such as pressure, dwell time and the solidification point (Sp) determined can be seen in Table 1. The dependence of the melamine solidification point on the particular prevailing ammonia partial pressure is shown in FIG. 1.

TABLE 1

| Example | p (bar) | h | Sp (° C.) |
|---|---|---|---|
| 1 | 350 | 6 | 294 |
| 2 | 300 | 6 | 300 |
| 3 | 250 | 6 | 306 |
| 4 | 200 | 6 | 317 |
| 5 | 150 | 6 | 328 |
| 6 | 110 | 6 | 331 |

EXAMPLES 7–19

9.9 g of melamine having a melam content of 1300 ppm, 0.1 g of melem and the amount of ammonia required to achieve the pressure $p_1$ desired prior to the depressurization were introduced into a laboratory autoclave having a volume of 70 ml. The autoclave was then brought to a temperature $T_1$, cooled if appropriate in x minutes to a temperature $T_2$ and kept at this temperature for $t_1$ minutes. The pressure was then rapidly reduced to a defined pressure $p_2$ and then, if appropriate, kept for $t_2$ minutes under the then-prevailing reaction conditions.

When this process was complete, the mixture was abruptly cooled and depressurized in the water bath and the melamine obtained was analyzed.

The process parameters such as pressure $p_1$ and $p_2$, temperature $T_1$ and $T_2$, cooling time from $T_1$ to $T_2$ in x minutes, dwell times $t_1$ and $t_2$, and the final content of melem (ME) and melam (MA) can be seen in Table 2.

TABLE 2

| Ex. | $p_1$ (bar) | $T_1$ (° C.) | x (min) | $T_2$ (° C.) | $t_1$ (min) | $p_2$ (bar) | $t_2$ (min) | ME ppm | MA ppm |
|---|---|---|---|---|---|---|---|---|---|
| 7 | 300 | 310 | 0 | 310 | 120 | 150 | 0 | 40 | <300 |
| 8 | 250 | 320 | 0 | 320 | 120 | 150 | 0 | 65 | 350 |
| 9 | 250 | 370 | 60 | 320 | 120 | 35 | 0 | 190 | 400 |
| 10 | 250 | 370 | 60 | 20 | 120 | 50 | 5 | 80 | 410 |
| 11 | 250 | 370 | 60 | 320 | 120 | 150 | 5 | 80 | 500 |
| 12 | 250 | 370 | 60 | 320 | 120 | 150 | 5 | 45 | 310 |
| 13 | 250 | 370 | 60 | 320 | 30 | 150 | 5 | 25 | <300 |
| 14 | 250 | 370 | 60 | 320 | 10 | 50 | 5 | 65 | <300 |
| 15 | 250 | 370 | 30 | 320 | 10 | 50 | 5 | 185 | 530 |
| 16 | 250 | 370 | 60 | 320 | 10 | 150 | 5 | 50 | <300 |
| 17 | 250 | 370 | 30 | 320 | 10 | 150 | 5 | 50 | <300 |
| 18 | 250 | 370 | 7 | 320 | 10 | 150 | 5 | 45 | <300 |
| 19 | 200 | 335 | 0 | 335 | 120 | 150 | 0 | 220 | 440 |

EXAMPLES 20–36 x g of melamine ($M_0$) having a melam content ($Ma_0$) of 1300 ppm and y g of melem ($ME_0$), and the amount of ammonia required to achieve the pressure $p_1$ desired prior to the depressurization, were introduced into a laboratory autoclave A1 having a volume of 100 ml. The autoclave was then brought to a temperature of 370° C. ($T_1$) and kept at $T_1$ for $t_1$ minutes. The autoclave was then cooled to a temperature $T_2$ in $z_1$ minutes and kept at this temperature for $t_2$ minutes.

In Examples 20–32, subsequently thereto, the melamine situated in A1 was sprayed into a laboratory autoclave A2 having a volume of 1000 ml which was kept at a temperature of $T_3$ and a pressure $p_3$.

In Examples 33 and 34, the temperature $T_2$ in the autoclave A1 was decreased to the temperature $T_{2s}$, in $t_{2s}$ minutes. Simultaneously with this, the temperature $T_3$ in the autoclave A2 was decreased to the temperature $T_{2s}$ and the pressure was set to the value of $p_3$ and the melamine from A1 was sprayed into A2.

In Examples 35 and 36, only a portion of the liquid melamine was sprayed from the autoclave A1 into the autoclave A2, by a valve in the line between A1 and A2 being briefly opened and closed again. This kept the pressure drop in A1 and the pressure increase in A2 low.

After the product transfer, the temperature $T_2$ in A1 changed to a value $T_{2.1}$, and the pressure $p_1$ to a value of $p_2$. In the autoclave A2, the temperature $T_3$ changed to a value $T_{3.1}$ and the pressure $p_3$ to a value $p_{3.1}$.

The melamine ($M_1$) remaining in A1 was cooled to a temperature $T_4$ in $z_2$ minutes, then depressurized, rapidly cooled and analyzed ($ME_1$, $MA_1$).

The melamine ($M_2$) sprayed into A2 was cooled to a temperature $T_5$ in $z_3$ minutes, depressurized, rapidly cooled and analyzed ($ME_2$, $MA_2$).

The process parameters such as pressure $p_1$, $p_2$, $p_3$ and $p_{3.1}$, temperature $T_1$, $T_2$, $T_{2.1}$, $T_{2s}$, $T_{3.1}$, $T_4$ and $T_5$, cooling time $z_1$, $Z_2$ and $Z_3$ minutes, dwell times $t_1$, $t_{2s}$ and the initial ($M_0$) and final ($M_1$, $M_2$) weights of melamine, the initial melem content ($ME_0$) and the final contents of melem ($ME_1$, $ME_2$) and melam ($MA_1$, $MA_2$) can be seen in Table 3.

TABLE 3

| | Autoclave A1 ($T_1$ = 370° C.) prior to product transfer | | | | | | | | |
|---|---|---|---|---|---|---|---|---|---|
| Example | $xM_0$ (g) | $yME_0$ (g) | $p_1$ (bar) | $t_1$ (min) | $z_1$ (min) | $T_2$ (° C.) | $t_2$ (min) | $T_{2s}$ (° C.) | $t_{2s}$ (min) |
| 20 | 9.9 | 0.1 | 250 | 0 | 60 | 320 | 10 | | |
| 21 | 9.9 | 0.1 | 250 | 0 | 60 | 315 | 10 | | |
| 22 | 9.9 | 0.1 | 250 | 0 | 60 | 310 | 10 | | |
| 23 | 9.9 | 0.1 | 350 | 0 | 60 | 300 | 10 | | |
| 24 | 29.7 | 0.3 | 250 | 90 | 60 | 320 | 10 | | |
| 25 | 19.8 | 0.2 | 250 | 120 | 60 | 320 | 10 | | |
| 26 | 19.8 | 0.2 | 250 | 120 | 60 | 320 | 10 | | |
| 27 | 9.9 | 0.1 | 300 | 0 | 60 | 315 | 10 | | |
| 28 | 9.9 | 0.1 | 200 | 0 | 60 | 330 | 10 | | |
| 29 | 9.9 | 0.1 | 350 | 0 | 60 | 303 | 10 | | |
| 30 | 9.9 | 0.1 | 350 | 0 | 60 | 310 | 10 | | |
| 31 | 9.9 | 0.1 | 200 | 60 | 60 | 330 | 10 | | |
| 32 | 19.8 | 0.2 | 250 | 120 | 60 | 320 | 10 | | |
| 33 | 9.9 | 0.1 | 250 | 60 | 53 | 320 | 120 | 312 | 24 |
| 34 | 9.9 | 0.1 | 250 | 60 | 41 | 330 | 120 | 314 | 32 |
| 35 | 9.9 | 0.1 | 265 | 120 | 69 | 316 | 0 | | |
| 36 | 9.9 | 0.1 | 260 | 120 | 59 | 317 | 0 | | |

| | Autoclave A1 after product transfer | | | | | |
|---|---|---|---|---|---|---|
| Example | $T_{2.1}$ (° C.) | $p_2$ (bar) | $M_1$ (g) | $T_4$ (° C.) | $z_2$ (min) | $ME_1$ (ppm) | $MA_1$ (ppm) |
| 20 | 307 | 90 | 5.5 | 245 | 13 | 20 | <300 |
| 21 | 285 | 85 | 7.0 | RT | 1 | 20 | <300 |
| 22 | 275 | 85 | 8.0 | 250 | 14 | 20 | <300 |
| 23 | 270 | 50 | 4.0 | 250 | 4 | <20 | <300 |
| 24 | 326 | 175 | 22.0 | 280 | 14 | <20 | <300 |

TABLE 3-continued

| | | | | | | | |
|---|---|---|---|---|---|---|---|
| 25 | 304 | 70 | 1.0 | 280 | 6 | 55 | 490 |
| 26 | 307 | 80 | 10.5 | 280 | 13 | 20 | <300 |
| 27 | 294 | 80 | 3.0 | 280 | 12 | 25 | <300 |
| 28 | 314 | 80 | 1.2 | 80 | 18 | <20 | 380 |
| 29 | 274 | 60 | 3.5 | 250 | 8 | <20 | 370 |
| 30 | 275 | 65 | 1.5 | 250 | 4 | <20 | <300 |
| 31 | 306 | 50 | 1.5 | 280 | 8 | 100 | 800 |
| 32 | 302 | 65 | 1.0 | 280 | 10 | 50 | 630 |
| 33 | 292 | 80 | 4.9 | 300 | 10 | <20 | <300 |
| 34 | 295 | 80 | 0.8 | 300 | 6 | <20 | <300 |
| 35 | 311 | 220 | 3.8 | 300 | 6 | <50 | 800 |
| 36 | — | 235 | 3.2 | 300 | 6 | <50 | 820 |

Autoclave A2

| Ex. | $T_3$ (° C.) | $p_3$ (bar) | $T_{3.1}$ (° C.) | $p_{3.1}$ (bar) | $M_2$ (g) | $T_5$ (° C.) | $z_3$ (min) | $ME_2$ (ppm) | $MA_2$ (ppm) |
|---|---|---|---|---|---|---|---|---|---|
| 20 | 277 | 52 | 284 | 79 | 3.5 | 250 | 12 | 75 | <300 |
| 21 | 280 | 51 | 282 | 76 | 2.7 | RT | r | 75 | 600 |
| 22 | 281 | 52 | 282 | 76 | 1.1 | 250 | 8 | 55 | 650 |
| 23 | 280 | 0 | 280 | 40 | 6.0 | 250 | 12 | 60 | 1100 |
| 24 | 320 | 6 | 320 | 15 | 3.0 | 280 | 15 | 40 | 1600 |
| 25 | 300 | 40 | 309 | 68 | 15.5 | 280 | 8 | 95 | 360 |
| 26 | 302 | 50 | 306 | 74 | 8.0 | 280 | 11 | 70 | 540 |
| 27 | 282 | 40 | 285 | 72 | 4.5 | 280 | 4 | 20 | 780 |
| 28 | 302 | 50 | 304 | 72 | 3.8 | 280 | 12 | 65 | 650 |
| 29 | 280 | 17 | 280 | 60 | 5.5 | 250 | 10 | 20 | 100 |
| 30 | 300 | 20 | 300 | 62 | 4.5 | 280 | 5 | 25 | 770 |
| 31 | 298 | 20 | 300 | 48 | 6.5 | 280 | 12 | 110 | 1000 |
| 32 | 300 | 30 | 305 | 62 | 16.0 | 280 | 11 | 45 | 790 |
| 33 | 312 | 52 | 312 | 78 | 2.9 | 280 | 15 | <20 | <300 |
| 34 | 314 | 51 | 314 | 76 | 6.2 | 280 | 15 | 20 | 300 |
| 35 | 316 | 53 | 316 | 57 | 2.8 | 280 | 15 | <20 | 400 |
| 36 | 280 | 55 | 280 | — | 3.2 | 275 | 3 | 40 | 750 |

RT to room temperature
r rapidly

What is claimed is:

1. A process for the preparation of substantially pure melamine, which comprises rapidly depressurizing liquid, ammonia-containing melamine from an ammonia partial pressure $p_1$ between 400 bar and 50 bar to an ammonia partial pressure $p_2$ between 200 bar and 20 bar pressure, where $p_1$ is always greater than $p_2$, at a temperature which is 0 to 60° C. higher than the melamine solidification point which is dependent on the particular prevailing ammonia partial pressure, but is below 350° C., higher pressures permitting a greater temperature interval from the melamine solidification point than lower pressures, whereby pure melamine separates out in solid form, whereupon, in any sequence, optionally further depressurizing the resultant product to atmospheric pressure, cooling to room temperature and isolating the substantially pure melamine.

2. The process as claimed in claim 1, wherein a melamine to be purified which is already present as melt or as liquid phase is brought to the ammonia partial pressure desired for the depressurization between about 400 to 50 bar, and to a temperature which is about 0 to 60° C. above the melamine solidification point dependent on the particular prevailing ammonia partial pressure.

3. The process as claimed in claim 2, wherein, in the process, the temperature is decreased.

4. The process as claimed in claim 2, wherein, in the process, the temperature is decreased at a cooling rate of 0.8 to 10° C./min.

5. The process as claimed in claim 2, wherein, in the process, ammonia is fed.

6. The process as claimed in claim 2, wherein the $NH_3/CO_2$ gas mixture forming in the urea conversion is separated off from the liquid melamine and the $CO_2$ dissolved in the liquid melamine is reduced by introducing gaseous ammonia.

7. The process as claimed in claim 1, wherein, before the depressurization, the liquid melamine is allowed to dwell for about 5 minutes to 20 hours.

8. The process as claimed in claim 1, wherein, before the depressurization, the liquid melamine is saturated with ammonia.

9. The process as claimed in claim 1, wherein the depressurization of the liquid, ammonia-containing melamine is carried out as closely as possible to or above the solidification point of the melamine dependent on the particular ammonia partial pressure.

10. The process as claimed in claim 1, wherein the liquid, ammonia-containing melamine is depressurized to a pressure between 20 bar and about 200 bar.

11. The process as claimed in claim 1, wherein the depressurization is performed in the vessel into which the liquid melamine was introduced.

12. The process as claimed in claim 1, wherein the depressurization is carried out by transferring or spraying into one or more vessels.

13. The process as claimed in claim 12, wherein an ammonia atmosphere is present in the vessels.

14. The process as claimed in claim 12, wherein approximately the same temperature prevails in the vessels as in the receptacle from in which depressurization is performed.

15. The process as claimed in claim 12, wherein, after the depressurization, the then solid melamine is allowed to dwell at a pressure between 200 bar and 20 bar for about 1 minute to 20 hours.

16. The process as claimed in claim 1, wherein, after the depressurization, the then solid melamine is allowed to dwell at a temperature below about 290° C.

17. The process as claimed in claim 1, wherein the then solid melamine is allowed to dwell at a temperature between about 280 and 250° C.

18. The process as claimed in claim 1, wherein the already solid melamine is cooled to room temperature by quenching with a cold, liquid medium.

19. The process as claimed in claim 1, wherein it is carried out continuously.

20. The process as claimed in claim 1, wherein it is carried out immediately downstream of a melamine high-pressure process.

21. The process as claimed in claim 1, wherein the melamine to be purified which is initially present as solid is heated at an ammonia partial pressure between about 400 and 50 bar, to a temperature which is about 0 to 60° C. above the melamine solidification point dependent on the particular prevailing ammonia partial pressure.

* * * * *